United States Patent [19]

DeVries

[11] Patent Number: 4,526,515

[45] Date of Patent: Jul. 2, 1985

[54] FLUID PUMPING ASSEMBLY INCLUDING A PREPACKAGED FLUID CIRCUIT MODULE

[75] Inventor: James H. DeVries, McHenry, Ill.

[73] Assignee: Baxter Travenol Laboratories, Inc., Deerfield, Ill.

[21] Appl. No.: 424,819

[22] Filed: Sep. 27, 1982

Related U.S. Application Data

[60] Division of Ser. No. 100,975, Dec. 6, 1979, Pat. No. 4,379,452, which is a continuation of Ser. No. 843,223, Oct. 18, 1977, abandoned.

[51] Int. Cl.³ .................. F04B 43/12; F04B 45/08
[52] U.S. Cl. .................................... 417/63; 417/475; 604/6; 604/153
[58] Field of Search ............... 417/475, 476, 477, 474, 417/63; 604/4, 5, 6, 65, 153

[56] References Cited

U.S. PATENT DOCUMENTS

| | | | |
|---|---|---|---|
| 3,658,445 | 4/1972 | Pulman et al. | 417/474 |
| 3,963,023 | 6/1976 | Hankinson | 417/477 X |
| 3,967,627 | 7/1976 | Brown | 128/400 |
| 4,025,241 | 5/1977 | Clemens | 417/474 X |
| 4,184,815 | 1/1980 | Casson et al. | 417/477 |
| 4,197,847 | 4/1980 | Djerassi | 604/6 |

Primary Examiner—Richard E. Gluck
Attorney, Agent, or Firm—Paul C. Flattery; Daniel D. Ryan

[57] ABSTRACT

A fluid pumping assembly includes a prepackaged, self-contained fluid circuit module which is selectively movable by an operator into and out of operative association with one or more pump rotors of an associated apparatus. The module includes a housing which supports two or more flexible conduits, which together define a prearranged fluid circuit. Portions of the flexible fluid conduits are outwardly disposed from the housing in upright, freestanding positions, even when the module is out of operative association with the pump rotors. The upright portions are purposely arranged relative to each other to facilitate only a particular operative relationship between the fluid circuit and the pump rotors when the module is subsequently moved into operative association therewith.

14 Claims, 5 Drawing Figures

FLUID PUMPING ASSEMBLY INCLUDING A PREPACKAGED FLUID CIRCUIT MODULE

This is a division of application Ser. No. 100,975, filed Dec. 6, 1979, now U.S. Pat. No. 4,374,452, which is a continuation of application Ser. No. 843,223, filed Oct. 18, 1977 (now abandoned).

CROSS REFERENCE TO RELATED APPLICATIONS

This application is related to, and incorporates herein by reference U.S. Pat. No. 4,185,629, issued Jan. 29, 1980 and entitled METHOD AND APPARATUS FOR PROCESSING BLOOD and U.S. Pat. No. 4,146,172, issued Mar. 27, 1979 and entitled CENTRIFUGAL LIQUID PROCESSING SYSTEM.

BACKGROUND OF THE INVENTION

1. Field of the Invention

The present invention relates to a monitor and fluid circuit assembly utilized in an apparatus for processing whole blood and more specifically to a compact disposable monitor and fluid circuit assembly for collecting a desired blood component such as platelets.

2. Description of the Prior Art

Heretofore various apparatus have been proposed for processing whole blood and separating the same into the various components thereof. Such prior art apparatus have involved intervivos blood processing in which whole blood is taken from a live donor, separated within a processing system into its constituent components and a desired component is segregated for collection from the donor, followed by returning the remaining blood fluid to the donor. Typically, the blood components that are separated are plasma, red blood cells, white blood cells and platelets. An apparatus and process which are particularly adapted for separating platelets from whole blood are described hereinafter. Such a process is commonly referred to as plateletpheresis.

Apparatus for carrying out intervivos blood processing that have been utilized in the past, have typically included a separation chamber within which whole blood from a donor is subjected to a centrifugal force. This is typically accomplished in a centrifuge device. Because of difference in densities the various blood components will congregate in different zones at different radial distances from the center of rotation of the separation chamber. Then, collection ports in the chamber are utilized to remove the blood components from the various zones in the separation chamber for storage or recirculation.

Heretofore such devices have required various fluid couplings and pressure monitor devices which must be thoroughly cleaned after each use and/or parts of the fluid system or circuit may be replaced.

As will be described in greater detail hereinafter, the present invention provides a monitor and fluid circuit assembly which can be easily mounted on and connected to a blood processing apparatus and easily detached therefrom for separation of a blood component collection bag, e.g., a platelet bag. Also the assembly is made of inexpensive plastic materials such that the assembly minus the collection bag can be discarded.

SUMMARY OF THE INVENTION

The invention provides a fluid pumping assembly comprising an apparatus which includes at least one pump rotor. The assembly also includes a prepackaged, self-contained fluid circuit module which is selectively movable by an operator into and out of operative association with the pump rotor. The module comprises an array of flexible conduits defining a prearranged fluid circuit, portions of which are carried within the confines of a hollow housing. A preselected portion of at least two of the conduits extends outwardly of the housing and forms a loop positioned to interfit with the pump rotor when the module is properly positioned on the apparatus. This arrangement facilitates only the desired operative contact between the fluid circuit and the pump rotor.

In one embodiment, a pair of loops are concentrically positioned to accommodate simultaneous operative contact with a single pump rotor.

In one embodiment, a pair of loops are positioned in a spaced, noncontiguous relationship to accommodate separate operative contact with a spaced pair of pump rotors.

By virtue of the invention, the possibilities of an incorrectly arranged flow system or an incorrect pump connection are all but eliminated. The invention significantly simplifies the handling of fluid circuits, particularly complex ones, such as those associated with blood processing assemblies.

In one embodiment, the module includes, as an integral part thereof, various containers of fluid and/or various fluid receiving receptables. This arrangement provides for an essentially "closed" fluid flow system. This further simplifies the handling of complex fluid systems and at the same time protects significant portions of the fluid flow system from contamination with the atmosphere.

DESCRIPTION OF THE PREFERRED EMBODIMENT

Figure 1:
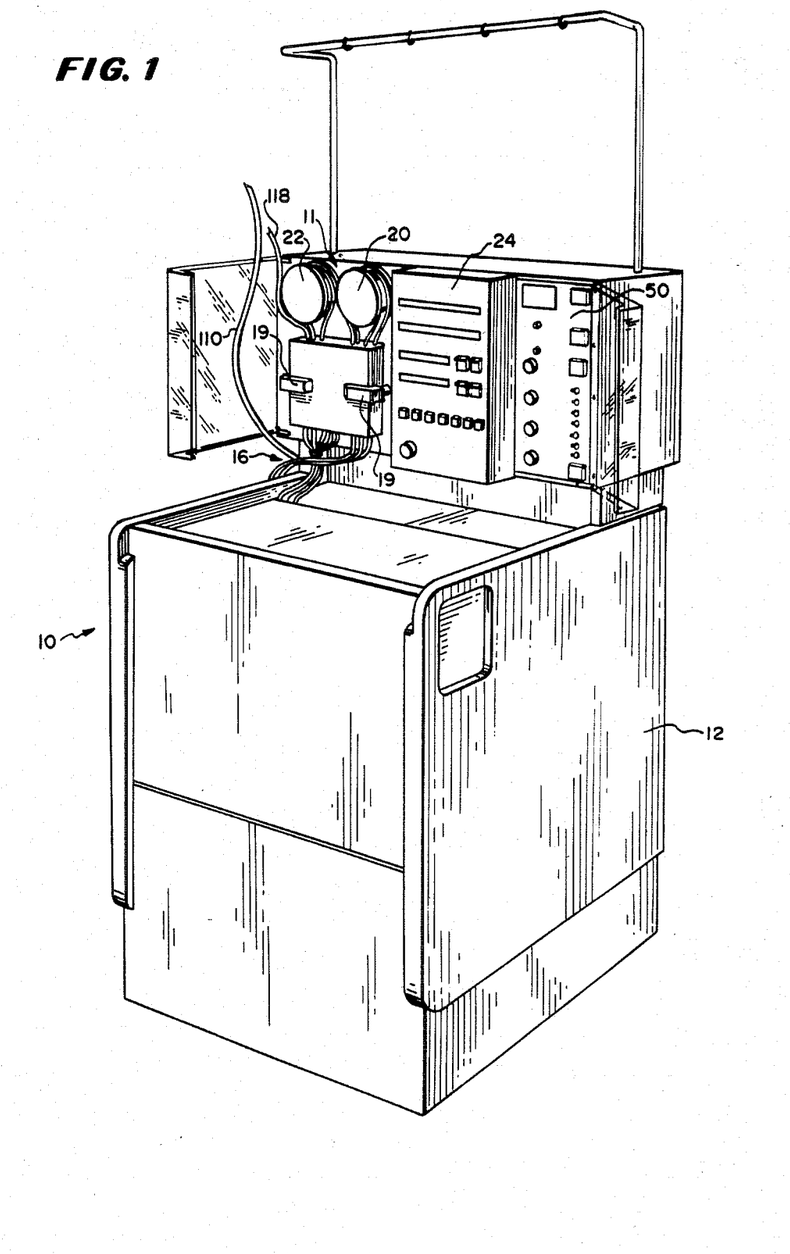
FIG. 1 is a perspective view of the apparatus with which the monitor and fluid circuit assembly of the present invention is used.

Referring now to the drawings in greater detail, a blood processing apparatus is shown in, and generally identified by the reference numeral 10 in, FIG. 1. The apparatus 10 includes the monitor and fluid circuit assembly, or module, of the present invention which is fully shown in, and identified by reference numeral 11 in, FIG. 4. The apparatus 10 further includes a centrifuge device hidden from view within the cabinet 12. The centrifuge device is shown schematically in FIG. 3 and identified therein by reference numeral 14. For further details of the construction and operation of the centrifuge device 14, reference is made to U.S. Pat. No. 4,146,172 entitled: CENTRIFUGAL LIQUID PROCESSING SYSTEM, the disclosure of which patent is incorporated herein by reference.

Figure 3:
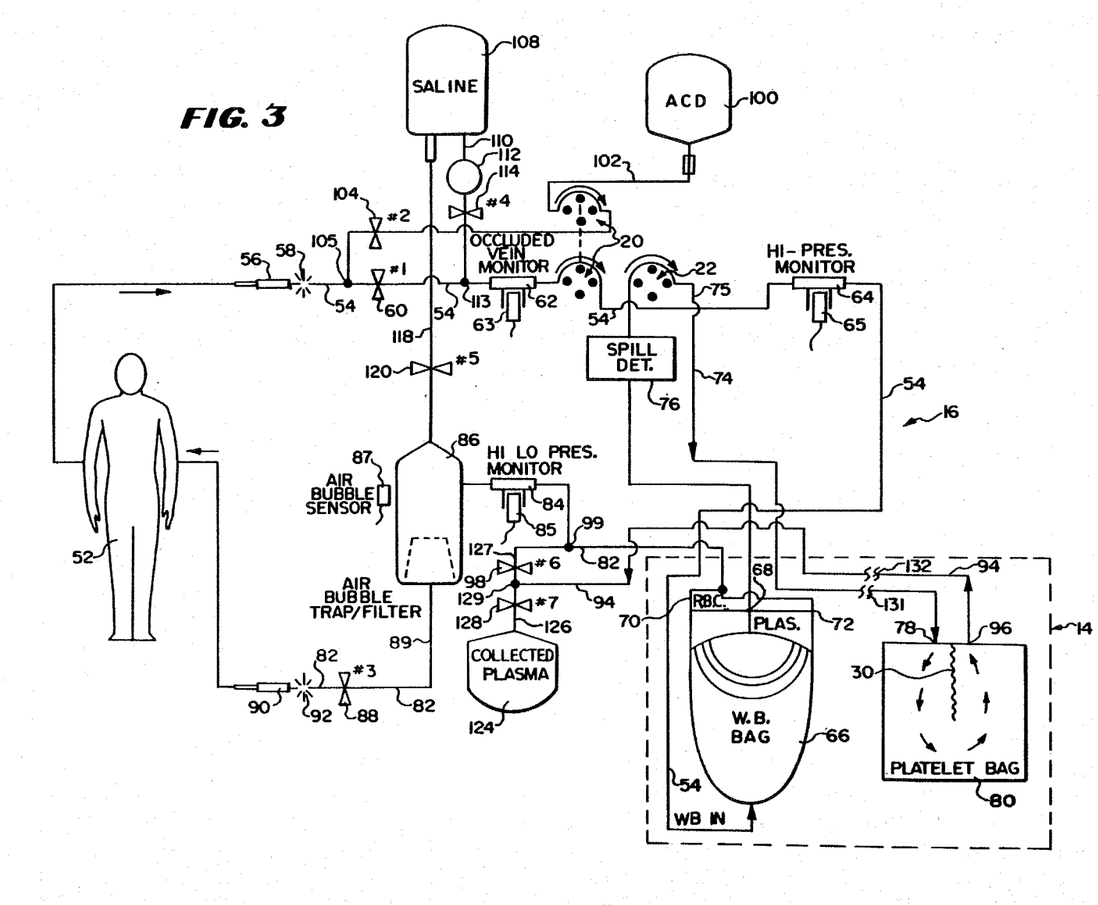
FIG. 3 is a schematic block flow diagram of the fluid circuit of the assembly.

The monitor and fluid circuit assembly 11 includes a fluid circuit which is generally identified by the reference numeral 16 in FIG. 1 and which is best shown schematically in FIG. 3. As will be described in detail in connection with the description of FIGS. 3 and 4, the fluid circuit 16 includes a plurality of flexible plastic tubings which form fluid couplings between various parts of the fluid circuit 16. These tubings are received through a holder or housing 18 which forms part of assembly 11 and which as monitor devices mounted therein.

Figure 2:
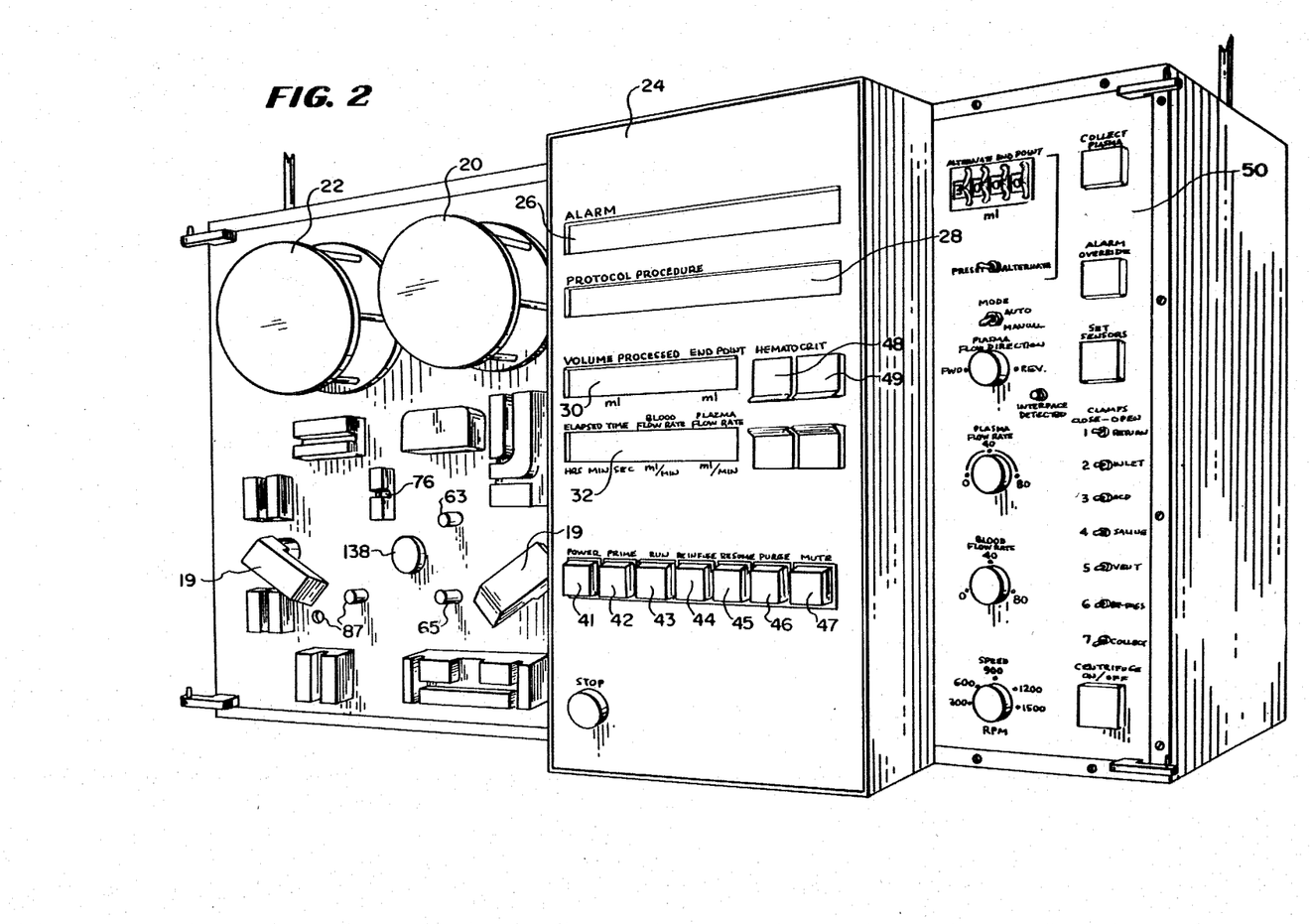
FIG. 2 is an enlarged perspective view of the upper portion of the apparatus shown in FIG. 1 with the monitor and fluid circuit assembly of the present invention removed.

As shown in FIGS. 1 and 2, several loops of the tubing (54,74,102 in FIGS. 3 and 4) are received over, in tight contact with, and form part of two peristaltic pumps 20 and 22. As will be described in greater detail hereinafter, the pump 20 is referred to as a first or whole blood pump and the pump 22 is referred to as a second or plasma pump. The whole blood pump 20 is utilized for withdrawing whole blood from a donor whereas the plasma pump 22 is utilized to move plasma from one chamber to another chamber within the centrifuge device 14 (FIG. 3).

The apparatus 10 also includes a display panel 24 including several windows for indicating information useful to an operator. In this respect, an alarm window 26 indicates a malfunction of the apparatus 10 or a condition occurring within the fluid circuit 16 of the apparatus 10. Also there is a window 28 indicating the blood component which is being collected, a window 30 indicating volume processed and end point and a window 32 indicating the elapsed time of operation of the apparatus 10, the flow rate of the whole blood and the flow rate of platelet rich plasma.

A number of push buttons 41–47 are provided for controlling various phases of operation of the apparatus 10, as well as windows 48 and 49 on the display panel 24 for indicating the hematocrit of the donor.

Additionally, the apparatus 10 includes a manual control panel 50 which, as best shown in FIG. 2, includes a plurality of knobs and switches for manual operation of the apparatus 10. The legends on the manual control panel 50 generally identify the various toggle switches and push button switches, the purpose of which will become apparent from the detailed description of the operation of the apparatus 10 set forth below.

Referring now to FIG. 3 there is illustrated therein a block schematic diagram of the fluid circuit 16. As shown, the circuit 16 includes a first fluid coupling or tubing 54 adapted to be coupled to a vein in one arm of a donor 52 by meeans of a hypodermic needle 56 which is injected into the arm. If desired a fluid clamp 58 (shown schematically) can be provided on the tubing 54. The first tubing 54 has associated therewith a solenoid operated clamp 60 forming valve #1. The tubing 54 then has series coupled thereto an occluded vein monitor device 62 with an associated sensor 63. Then, the first tubing 54 extends over and forms part of the peristaltic pump 20 and is series coupled to a high pressure monitor device 64 with an associated sensor 65. From the monitor device 64 the first tubing 54 extends into the centrifuge device 14 and to the bottom inlet of a first compartment or receptacle 66 which is identified as a whole blood bag and which defines therein a whole blood separation chamber.

The receptable 66 has a first outlet 68 at the center thereof adjacent a zone in the receptacle 66 where platelet rich plasma congregates. Receptacle 66 also has two outlets 70 and 72 at the upper corners thereof where red blood cells congregate. Outlet 68 provides not only an outlet for platelet rich plasma but also a return inlet for platelet rich plasma which is "contaminated" (mixed) with red blood cells when there is a spillover of red blood cells out of outlet 68.

The outlet 68 of the first receptacle 66 is coupled to a second fluid coupling or tubing 74 which extends to a loop 75 thereof located exterior of the centrifuge device 14 and which loop extends about and forms part of the peristaltic pump 22. Also, positioned adjacent a transparent or translucent section of the loop 75 which extends out of the centrifuge device 14 is a spill detector device 76 which is an optical sensor for sensing a spillover of red blood cells mixed with platelet rich plasma. The device 76 includes a light emitting diode (LED) such as an infra red LED sold by Texas Instrument under type numer TIL 32 and a phototransistor, such as a phototransistor sold by Texas Instrument under type number TIL 81. The second tubing 74 then goes back into the centrifuge device 14 and is coupled to an inlet 78 of a second compartment or receptacle 80 which is identified as platelet bag defining a chamber therein where platelets are separated from plasma.

A third fluid coupling or tubing 82 is connected to the outlets 70 and 72 of the first receptacle 66 and to the donor through a high/low pressure monitor device 84 with associated sensor 85 and an air bubble trap/filter 86 and associated air bubble sensor 87 which monitor device 84 and filter 86 are coupled in series in the third tubing 82. Also another solenoid clamp 88 is associated with a portion 89 of the tubing 82 coming out of the air bubble trap/filter 86 and forms valve 83. The sensor 87 can be optical or ultrasonic.

The end of third tubing 82 is connected to a hypodermic needle 90 for injection into the other arm of the donor and, if desired, a fluid clamp 92 (shown schematically) can be provided in tubing 82 ahead of the needle 90.

The fluid circuit 16 further includes a fourth fluid coupling or tubing 94 which is with an outlet 96 of the second receptacle 80 and joins a fifth fluid coupling or tubing 127 in which a solenoid operated clamp 98 forming valve #6 is located and which forms a junction 99 with the third tubing 82.

The fluid circuit 16 also includes a first container 100 of anti-coagulant such as Acid Citrose Dextrose (ACD) which is coupled by a first auxiliary fluid coupling or tubing 102 about (and forming part of) the peristaltic pump 20 and through a solenoid operated clamp 104 defining valve #2 to a junction 105 with the first tubing 54 between the needle 56 and valve #1.

With this arrangement of the first tubing 54 and the first auxiliary tubing 102 passing over the same peristaltic pump 20, the mixing of anti-coagulant with whole blood and the withdrawing of whole blood from the donor is achieved essentially simultaneously. Also, the ratio of the cross sectional area of the interior of the tubing 54 to the cross sectional area of the interior of the tubing 102 is chosen to obtain a desired mixture of anti-coagulant to whole blood. This ratio is preferably 8 to 1 thereby to obtain an 8 to 1 ratio of whole blood to anti-coagulant.

The apparatus 10 and fluid circuit 16 further include a second container 108 of saline solution which is connected by means of a second auxiliary coupling or tubing 110 through a drip chamber 112 and a solenoid operated clamp 114 defining valve #4 to the first tubing 54 at a junction 115 between solenoid operated clamp 60 and the occluded vein monitor device 62. The container 108 of saline solution is also coupled by means of a third auxiliary fluid coupling or tubing 118 through a solenoid clamp 120 forming valve #5 to the top of the air bubble trap/filter 86.

The apparatus 10 and the fluid circuit 16 thereof further include a third receptacle or compartment 124 located outside of the centrifuge device 14 for collecting plasma. This receptable 124 is coupled to the fourth tubing 94 at junction 129 by branch coupling or tubing 126 through a solenoid operated clamp 128 forming solenoid valve #7.

The operation of the apparatus 10 for processing whole blood through the fluid circuit 16 will now be briefly described with reference to FIG. 3.

First of all, a donor is chosen who will be a healthy person donating platelets and who will be treated much like a blood donor. When the apparatus 10 is ready, two venipunctures will be made, one in each arm, with needles 56 and 90.

Valve #1 is opened first to allow saline to purge the input needle 56 prior to injection in the donor. Then valves #1, #2, #5 and #7 are closed. Valves #3, #4 and #6 are open.

Then, saline is pumped by the first pump 20 through the fluid circuit 16 until no more air bubbles are sensed by the air bubble sensor 87, i.e., until saline is sensed. Next, the second pump 22 is started and saline is pumped through the platelet receptacle 80. Since the centrifuge device 14 is not running at this time, the receptacles 66 and 80 are not filled to capacity. Air is expelled through the needle 90.

After a short time, e.g., one to five minutes the platelet receptacle/bag 80 will be filled, all air expelled and saline fills the entire system, i.e., fluid circuit 16 up to valve #3. When saline is sensed by detector #7, valve #3 is closed and valve #5 is opened. After a period of recirculation of saline, pumps 20 and 22 are stopped and valve #3 is opened.

Parenthetically, during this priming operation, the air bubble sensor 87 is checked when air bubbles are flowing through the air bubble trap/filter 86 to make sure that sensor 87 is working properly and then later, sensor 87 is checked to make sure there are no more bubbles after the system is filled with saline.

Now the needles 56 and 90 are inserted into the arms of the donor 52 and valves #1, #2, #5 and #6 are open and valves #3 and #7 are closed.

With the needles 56 and 90 connected to the veins of a donor and the system full of saline, the pumps 20 and 22 are started and whole blood is pumped into the system and into the centrifuge device 14.

It will be noted that the tubings 54, 74, 82 and 94 extending into the centrifuge device 14 may be combined in an umbilicus (139 in FIG. 4) which is rotated at a speed ½ the speed of the centrifuge device 14 so that twisting is avoided and no fluid seals are required. This arrangement and operation of the centrifuge device 14 is more fully described in the patent entitled: CENTRIFUGAL LIQUID PROCESSING SYSTEM referred to above.

When approximately 120 milliliters of whole blood has been pumped into the fluid circuit 16, most of the saline solution will have been pumped back into the container 108. Valve #3 is now opened so that processed blood fluid mixed with some saline solution can now be returned to the donor.

Also, if the plasma collect button had been pushed, valve #6 is closed and valve #7 opened and a desired amount of plasma will be collected while whole blood is being processed through the fluid circuit 16 after which valve #7 is closed and valve #6 is opened.

After starting pumps 20 and 22 no further operator attention is required until the end of the run.

As the whole blood is being drawn into the fluid circuit 16 and into the separation chamber in the receptacle 66, the centrifugal force acting on the receptable 66 causes separation of the components of the whole blood. In this respect, platelet rich plasma congregates in a zone at the top of the receptacle 66 adjacent to outlet 68 and red blood cells congregate at the upper corners of the receptacle 66 adjacent outlets 70 and 72. This is achieved by the particular construction and orientation of the receptacle 66 which is described in more detail in U.S. Pat. No. 4,146,172 referred to above.

In one working example of the apparatus 10, the volumetric displacement of pump 20 is started at an initial speed and increased by 1 milliliter per minute after each 120 milliliters of whole blood, has been processed through the fluid circuit 16 without a spillover of red blood cells. However, when a spillover of red blood cells from the receptacle 66 is sensed by the spill detector device 76, pump 22 is stopped and then reversed to return the mixture of platelet rich plasma and red blood cells to receptacle 66. Then the speed of the first pump 20 is decreased by one milliliter per minute and the speed of pump 22 is changed proportionately. Both pumps are then run in the normal direction (forward) until another 120 milliliters of whole blood is processed without a spillover. If a spillover is not detected by the device 76, the speed of the second pump 22 is then increased by 0.25 milliliters per minute for each 120 milliliters of blood processed without a spillover until a spillover is detected. Then when a spillover is detected, the pump 22 is again stopped and reversed to return the spillover mixture to receptacle 66. Next the volumetric displacement of the second pump 22 is decreased by 0.25 milliliters per minute, the pump 22 speed reversed back to forward speed and this process repeated until the end point of the run is reached. By the end point is meant that the processing of approximately 3 liters of whole blood has been completed. Operated in this manner, the apparatus 10 provides a highly efficient and effective separation of platelet rich plasma from whole blood.

Platelet rich plasma which is withdrawn from the receptacle 56 is passed through the platelet receptacle or bag 80. In view of the centrifugal force acting on the bag 80, platelet sedimentation on the side of the bag 80 takes place while plasma flows through the bag 80. This flow is enhanced by pinching the bag 80 in the center thereof as indicated by the wavy line 130 in FIG. 3. This results in a flow of plasma through the bag or receptacle 80 in the manner indicated by the arrows shown in FIG. 3.

The plasma that exits from the bag 80 flows through the tubing 94 and recombines at the junction 99 with the red blood cell rich blood fluid flowing through the tubing 82. The recombined platelet poor blood is then passed through the high/low pressure monitor 84 and air bubble trap/filter 86 and back into the donor 52 though the needle 90.

Once a desired amount of whole blood, i.e., 3 liters of whole blood, has been processed, valves #1 and #2 are closed and valve #4 is opened to allow saline to flow into the system, i.e., fluid circuit 16. The saline will then purge the remaining amount of blood in the fluid circuit 16 and push it back into the donor. Then after a sufficient amount of saline has been pumped into the system the centrifuge device 14 is stopped. About 3 milliliters of blood fluid is left in the system and can be returned to the donor by allowing a short overrun of the pump 20. The cabinet 12 now can be opened to sever tubings 74 and 94 such as with a heating element as indicated by breaks 131 and 132 shown in FIG. 3. The sealed platelet receptacle/bag 80 with a minimum of plasma therein is taken out of the centrifuge device 14 and stored for use.

Figures 4, 5:
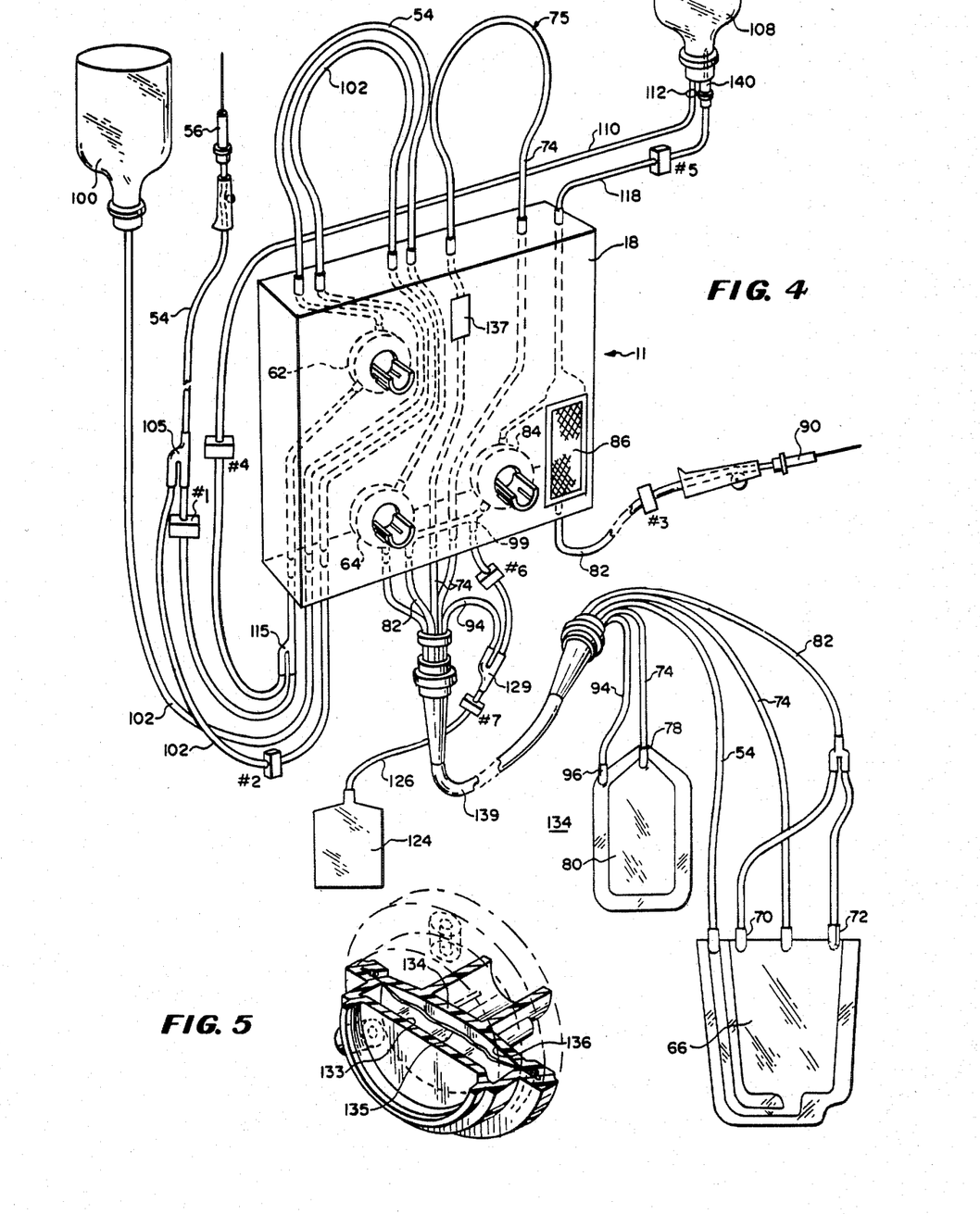
FIG. 4 is a perspective view of the monitor and fluid circuit assembly of the present invention.
FIG. 5 is a fragmentary perspective view of one of the monitor devices of the assembly.

Referring now to FIG. 4 there is illustrated therein the monitor and fluid circuit assembly 11 of the present invention. As shown this assembly 11 includes the holder or housing 18 through which all tubings except tubing 110 are received and held. As shown first and first auxiliary tubings 54 and 102 extend into the bottom of the holder 118 and perpendicularly out the top thereof to form outwardly bowed loops which are juxtaposed concentrically with each other. These loops extending from the top of the holder 18 of the tubings 54 and 102 are resiliently biased toward an upright freestanding position when the holder 18 is out of operative association with the apparatus 10. When the holder 18 is moved into operative contact with the appartus 10, the concentric freestanding loops of the tubings 54 and 102 are simultaneously received over, and form part of, the peristaltic pump 20. In a similar manner the second tubing 74 extends into the bottom of the holder 18 and perpendicularly out the top of the holder 18 to form the outwardly bowed loop 75 and then passes back to the holder 18. This loop 75 is resiliently biased toward an upright freestanding position when the holder 18 is out of operative association with the apparatus 10. The loop 75 is positioned in a spaced, noncontiguous relationship with each of the concentric loops of the tubings 54 and 102 so that, when the holder 18 is moved into operative association with the apparatus 10, the loop 75 is received over, and forms part of, the second pump 22 which is spaced from the pump 20. The valves #1–#7 are schematically shown by blocks. It will be understood that these valves #1–#7 are actually solenoid operated clamps as described above.

The pressure monitor devices 62, 64 and 84 are identical and only one will be described in connection with the breakaway view of one device shown in FIG. 5. As shown the device 62, 64 and 84 includes a flow through chamber 133 series connected in the associated tubing 54 or 84 and an air filled closed chamber 134 having a flexible diaphragm 135 forming part of one wall of the flow through chamber and an outer wall 136 which is situated adjacent the associated sensor 63, 65 or 85 which pressure transducers and which sense changes in pressure on the outer wall 136. The monitor devices 63, 65 or 85 and air bubble trap/filter 86 are all mounted in holder 18 in the positions shown in FIG. 4. Also each of the monitor devices 62, 64 and 84 has a hollow cylindrical protuberance extending therefrom for fitting about the side of a mating solid cylindrical pressure sensor 63, 65 or 85 which are shown in FIG. 2 where the holder 18 has been removed and not shown in FIG. 4 which only shows the assembly 11. Also, the transparent section of tubing 75 which is generally identified by reference numeral 137 in FIG. 4 will be positioned adjacent sensor 76 and the transparent section of the air bubble trap/filter 86 will be positioned adjacent the sensor 87 when the holder 18 is positioned on the upper portion of the apparatus 10 shown in FIG. 2 and the clamps 19 are moved to secure holder 18 in place. Note also that a sensor 138 (FIG. 2) of the apparatus 10 will sense when the holder 18 is in place.

The first, second, third, and fourth tubings 64, 74, 82 and 94 coming out of the holder 18 are passed through an umbilicus 139 which is received in a rotating holder of the centrifuge device 14 as described above.

The first and second containers 100 and 108 can form part of the assembly 18 and be secured to the tubings 102, 110 and 118 as shown or the assembly can merely include injection type coupling devices at the outer end of each of the tubings 102, 110 and 118 adapted for connection to one of the containers 100 and 108. Such a coupling device is shown injected through a membrane at the mouth of the container 108 and is generally identified by the reference numeral 140. Also these containers are typically made of a flexible, disposable, plastic material.

It will be understood that the holder 18 is made of an inexpensive and disposable material, e.g., plastic as are the tubings and the receptacles 66, 80 and 124. Likewise the monitor devices 62, 64 and 84 are made of an inexpensive plastic material so they can be readily disposed of once the assembly 11 has been utilized in the processing of whole blood to collect platelets and the platelet receptacle or bag 80 has been removed.

It will be understood that, excluding the holder 18, the assembly 11 constitutes the entire fluid circuit 16 of the apparatus 10. Also, with the arrangement of the monitor devices 62, 64 and 84 in the holder 18, as well as the positioning of the light transmitting tubing segment 137 and a light transmitting portion of a wall of the air bubble trap/filter 86 in the holder 18 as shown, a simple and compact monitor and fluid circuit assembly is provided which can be easily mounted in place by manipulation of the pivotal clamps 19 with the loops of the tubings 54, 75 and 102 received over, and forming part of, the peristaltic pump 20 and 22 and with the receptacles 66 and 80 inserted in the rotor of the centrifuge device 14 of the apparatus 10. Then when the processing of a predetermined amount of whole blood, e.g., 3 liters of whole blood, is completed the whole assembly 11 can be removed from the apparatus 10 and the tubings 94 and 74 above the receptacle 80 can be severed and sealed such as with a heating element at breaks 131 and 132 so that the platelet receptacle 80 can be removed from the assembly 11 and stored for future use.

From the foregoing description it will be apparent that the monitor and fluid circuit assembly 11 of the present invention has a number of advantages some of which have been described above and others of which are inherent in the invention. Accordingly, the scope of the invention is only to be limited as necessitated by the accompanying claims.

I claim:

1. A fluid pumping assembly comprising
an apparatus including at last two spaced apart pump rotors, and
a prepackaged, self-contained fluid circuit module including
housing means including means for removably positioning said housing means on said apparatus in a predetermined relationship with respect to said pump rotors,
flexible first conduit means extending through said housing means and defining a fluid pathway adapted for communication with a source of fluid, said first conduit means including a portion extending from and into said housing means to form a loop portion exterior of said housing means and disposed to interfit with a selected one of said pump rotors when said housing means is positioned in said predetermined relationship therewith, and flexible second conduit means extending through said housing means and defining a fluid pathway adapted for communication with a source of fluid, said second conduit means including a portion extending from and into said housing means to form a loop portion exterior of said housing means and disposed to interfit with the other one of said pump rotors when said housing means is positioned in said predetermined relationship therewith, whereby it is assured that each of said first and second conduit means will interfit only with the correct one of said pump rotors when said fluid circuit module is positioned on said apparatus.

2. A fluid pumping assembly according to claim 1 wherein said fluid circuit module further includes flexible first auxiliary conduit means extending through said housing means and defining a fluid pathway adapted for communication with a source of fluid, said first auxiliary conduit means including a portion extending from and into said housing means to form a loop portion exterior of said housing means and adjacently disposed concentrically with said loop portion of said first conduit means to interfit with said one peristaltic pump rotor.

3. A fluid pumping assembly comprising
an apparatus including at least one pump rotor,
a prepackaged, self-contained fluid circuit module including housing means including means for removably positioning said housing means on said apparatus in a predetermined relationship with respect to said peristaltic pump rotor, flexible first conduit means extending through said housing means and defining a fluid pathway adapted for communication with a source of fluid, said first conduit means including a portion extending from and into said housing means to form a loop portion exterior of said housing means and disposed to interfit with said pump rotor when said housing means is positioned in said predetermined relationship therewith, and flexible first auxiliary conduit means extending through said housing means and defining a fluid pathway adapted for communication with a source of fluid, said first auxiliary conduit means including a portion extending from and into said housing means to form a loop portion exterior of said housing means and adjacently disposed concentrically with said loop portion of said first conduit means to also interfit with said pump rotor when said first conduit means is interfitted therewith, whereby it is assured that each of said first and first auxiliary conduit means will simultaneously interfit with said pump rotor when said fluid circuit module is positioned on said apparatus.

4. A fluid pumping assembly according to claim 1 or 2 or 3 wherein each of said loop portions is resiliently biased toward an upright freestanding position when said module is out of association with said apparatus to accommodate said interfit with said respective pump rotor.

5. A fluid pumping assembly according to claim 1 or 2 wherein said apparatus further includes sensing means positioned adjacent to said pump rotors, and wherein said fluid circuit module includes at least one monitoring device carried by said housing means in flow communication with at least one of said conduit means, and wherein said housing positioning means is further operative for positioning said housing means on said apparatus with said monitoring device in operative contact with said sensing means.

6. A fluid pumping assembly according to claim 5 wherein each of said loop portions is resiliently biased toward an upright freestanding position when said module is out of association with said apparatus to accommodate said interfit with said respective pump rotor.

7. A fluid pumping assembly according to claim 1 or 2 wherein said fluid circuit module includes at least one container integrally joined in flow communication with at least one of said conduit means, said container thereby forming an integral part of said module.

8. A fluid pumping assembly according to claim 7 wherein said container includes a sealed container of fluid comprising the source of fluid for said conduit means integrally joined thereto.

9. A fluid pumping assembly according to claim 7 wherein said apparatus further includes sensing means positioned adjacent to said pump rotors, and wherein said fluid circuit module includes at least one monitoring device carried by said housing means in flow communication with at least one of said conduit means, and wherein said housing positioning means is further operative for positioning said housing means on said apparatus with said monitoring device in operative contact with said sensing means.

10. A fluid pumping assembly according to claim 7 wherein each of said loop portions is resiliently biased toward an upright freestanding position when said module is out of association with said apparatus to accommodate said interfit with said respective pump rotor.

11. A fluid pumping assembly according to claim 3 wherein said apparatus further includes sensing means positioned adjacently to said pump rotor, and wherein said fluid circuit module includes at least one monitoring device carried by said housing means in flow communication with at least one of said conduit means, and wherein said housing positioning means is further operative for positioning said housing means on said apparatus with said monitoring device in operative contact with said sensing means.

12. A fluid pumping assembly according to claim 3 or 11 wherein said fluid circuit module includes at least one container integrally joined in flow communication with at least one of said conduit means, said container thereby forming an integral part of said module.

13. A fluid pumping assembly according to claim 12 wherein said container includes a sealed container of fluid comprising the source of fluid for said conduit means integrally joined thereto.

14. A fluid pumping assembly according to claim 12 wherein each of said loop portions is resiliently biased toward an upright freestanding position when said module is out of association with said apparatus to accommodate said interfit with said respective pump rotor.

* * * * *